United States Patent [19]
Atwood et al.

[11] Patent Number: 4,598,765
[45] Date of Patent: Jul. 8, 1986

[54] SAMPLE CELL TEMPERATURE STABILIZER

[75] Inventors: John Atwood, Redding; Charles Helms, Trumbull; Raymond P. W. Scott, Wilton, all of Conn.

[73] Assignee: The Perkin-Elmer Corporation, Norwalk, Conn.

[21] Appl. No.: 576,585

[22] Filed: Feb. 3, 1984

[51] Int. Cl.$^4$ .................................. F25B 29/00
[52] U.S. Cl. ...................................... 165/66; 422/70
[58] Field of Search .................. 165/61, 66, 177; 422/70, 161; 73/61.1 C

[56] References Cited

U.S. PATENT DOCUMENTS

| | | | |
|---|---|---|---|
| 2,201,056 | 5/1940 | Seligman | 165/66 X |
| 3,273,356 | 9/1966 | Hoffman | 165/66 X |
| 3,799,250 | 3/1974 | Dyre | 165/66 X |
| 4,248,259 | 2/1981 | Kaartinen et al. | 165/61 X |
| 4,296,738 | 10/1981 | Kelton | 165/177 X |
| 4,479,727 | 10/1984 | Domingorena et al. | 165/66 X |

Primary Examiner—Albert W. Davis, Jr.
Assistant Examiner—Peggy Neils
Attorney, Agent, or Firm—F. L. Masselle; E. T. Grimes

[57] ABSTRACT

An apparatus for modifying the temperature of the effluent of a fluid stream entering a flow cell which includes a counterflow heat exchange between the outlet fluid and the inlet fluid and a thermally equilibrating the flow cell with the inlet fluid after it has passed through the counterflow heat exchange and before it enters the flow cell.

6 Claims, 1 Drawing Figure ered 4,598,765

SAMPLE CELL TEMPERATURE STABILIZER

BACKGROUND OF THE INVENTION

The present invention relates generally to a flow cell apparatus and, in particular, relates to such an apparatus for equilibrating the temperature of a fluid passing therethrough.

Sample flow cells are available in a variety of shapes, sizes and configurations. In addition, heat exchangers for use therewith are also known. The primary purpose of previous heat exchangers is merely to remove thermal energy from the flowing fluid containing the sample before it reaches the sample cell. Very often such a heat exchanger functions by transferring thermal energy to a working fluid, which can, of course, include a gas and which subsequently carries the transferred thermal energy away from its source. Alternatively, the heat may be transferred to the main structure of the instrument containing the sample flow cell. If this structure is relatively large and the heat carried by the flowing sample is relatively small, the heat may be dissipated to the environment. However, if the heat flow is relatively large, the entire instrument may be disturbed and result in inaccuracies.

Further, the extra path length and extra volume of the heat exchange tubing through which the flowing sample must pass causes remixing of adjacent but separate components in the flowing sample. The extent of remixing depends on the volume and length of the tubing through which it must pass. In applications such as liquid chromatography for example, where the separation of components is achieved at significant cost in time and apparatus, the partial remixing of the components in the heat exchanger can significantly reduce the performance of the apparatus.

For these reasons, it is important to effect any desired heat exchange with a minimum of length, and consequently volume, of tubing.

However, in many applications, the simple removal of thermal energy from the flowing sample is not as important as is the ability to equilibrate the temperature of the flowing fluid with the device through which the fluid passes.

One device where such equilibration is highly desirable is the flow cell of a liquid chromatography system. In a liquid chromatography system, the eluate of the separating column may be required by the particular analysis to exit at a rather elevated temperature. The eluate is conveyed, via a short connecting conduit, to a measuring flow cell. Often, a measuring light beam is passed through the flow cell and the intensity reduction of the light beam during its passage through the cell is a measure of the absorbance of the fluid passing therethrough. Frequently, if the difference in temperature between the eluate of the column and the body of the flow cell is excessive, unacceptable noise results in the detection mechanism. Hence, it is often desirable to reduce this temperature difference while employing a very short length and very small volume of heat exchange tubing.

One way to minimize the temperature difference between the flowing sample and the flow cell is to thermally isolate the flow cell from the main structure of the instrument and exchange heat between the fluid and the flow cell before the fluid enters the measurement part of the cell. This results in the temperature of the flow cell changing until it nearly equals that of the incoming fluid. However, if the sample is much hotter or much colder than the main structure of the instrument, difficulties of a different kind can result. Some of the difficulties are, the thermal expansion of the cell relative to its mounts, thermal convection of air around the cell, the formation of condensation on the cell windows, etc.

SUMMARY OF THE INVENTION

Accordingly, it is one object of the present invention to provide an apparatus for equilibrating the temperature of a fluid passing through a flow cell with the body of the flow cell before the fluid enters the cell without allowing the temperature of the cell to approach that of the incoming stream; without exchanging a significant amount of heat with the main structure of the instrument; and utilizing a minimal additional length and volume of tubing.

This object is achieved, at least in part, by using two different kinds of heat transfer. One kind for equilibrating the flowing stream with the cell body prior to it entering the cell body. The other kind being a counterflow heat exchanger in which the fluid exiting the flow cell exchanges heat with the incoming fluid before it reaches the equilibrating heat exchanger.

The counterflow heat exchanger causes the fluid leaving the flow cell to approach the temperature of the incoming fluid; hence, it carries away the excess heat of the incoming stream.

Concomitantly, the counterflow heat exchanger causes the incoming fluid to approach the temperature of the fluid leaving the flow cell, which is close to the temperature of the flow cell itself. Thus, before the incoming fluid reaches the equilibrating heat exchanger, it has already approached the temperature of the flow cell. Further, the tubing and volume required in the equilibrating heat exchanger is minimized, and the cell body temperature is not required to approach that of the incoming fluid.

Also, since the counterflow heat exchanger need not exchange heat with the main structure of the instrument, it is preferably constructed using the existing conduits with only a small additional length and volume to ensure intimate thermal contact therebetween.

Other objects and advantages will become apparent to those skilled in the art from the following detailed description read in conjunction with the appended claims and the drawing attached hereto.

BRIEF DESCRIPTION OF THE DRAWING

The single FIGURE of the drawing, not drawn to scale is a pictorial view, partially in section, of a flow cell apparatus embodying the principles of the present invention.

DETAILED DESCRIPTION OF THE INVENTION

Figure 1:
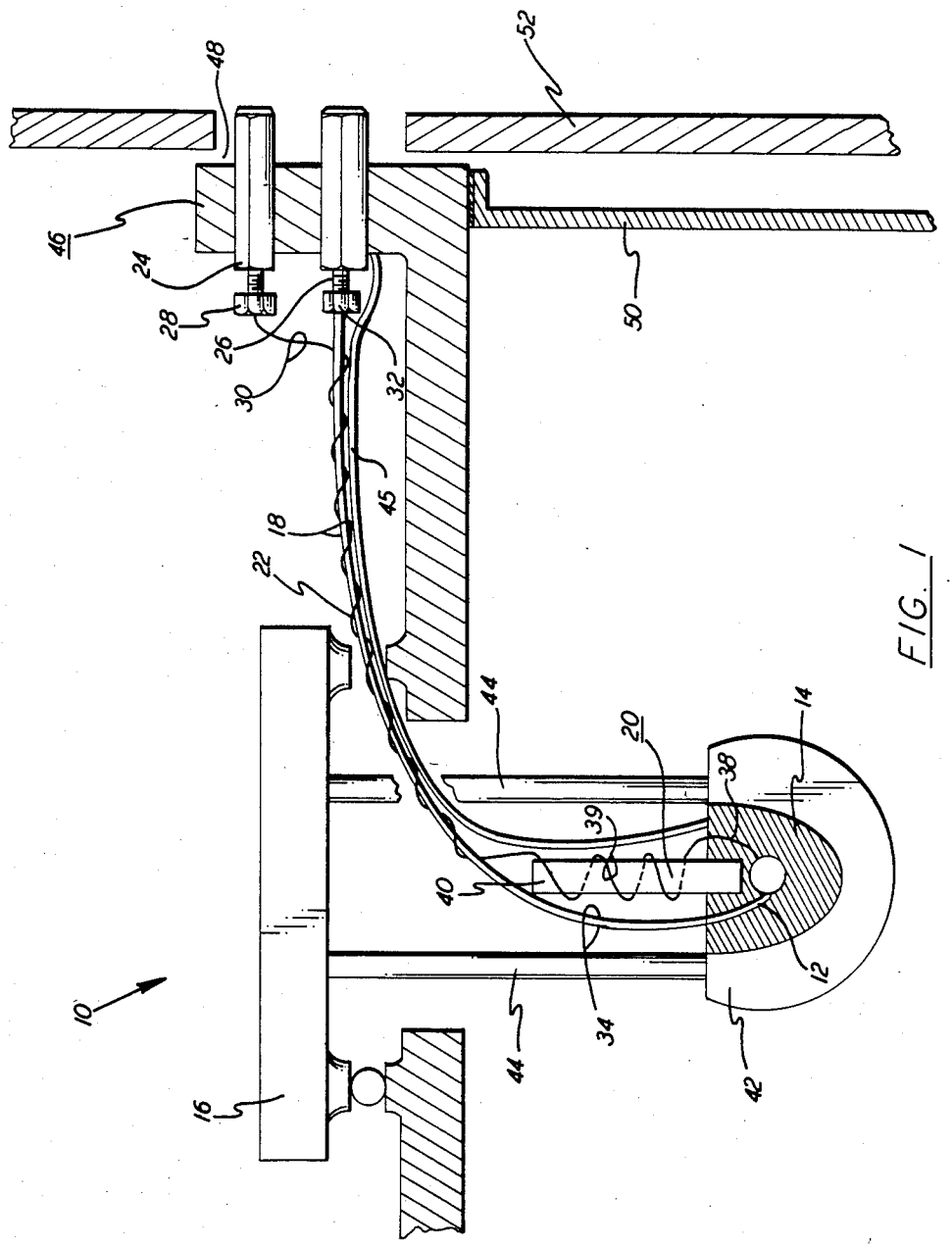

An assembly, generally indicated at 10 in the drawing and embodying the principles of the present invention, includes a flow cell 12 positioned within a flow cell housing 14. The assembly 10 includes a kinematic mounting mechanism 16 which ensures continual alignment between the flow cell 12 and the remainder of the optical components, not shown in the drawing. The assembly 10 further includes means 18 for modifying the temperature of the incoming fluid before it enters the flow cell 12. The assembly 10 includes a heat exchanger 18 which includes a temperature equilibrating rod 20 for exchanging heat between the incoming fluid and the cell body 12 and additionally includes coils 22 of the incoming fluid conduit around the outgoing conduit 34 for exchanging heat between the incoming fluid and the outgoing fluid.

The assembly 10 includes an inlet port 24 and an outlet port 26. The inlet port 24 is in fluid communication with an inlet fitting 28 via an inlet conduit 30. The outlet port 26 is in fluid communication with an outlet fitting 32 via an outlet conduit 34. The inlet conduit 30 is in thermal communication with the outlet conduit 34 over a majority of the length thereof and effectively constitutes the counterflow heat exchanging coil 22 between the entering and exiting fluids of the flow cell 12. Preferably, the inlet conduit 30 is helically wrapped about the outlet conduit 34 and, in the preferred embodiment, is bonded thereto via a thermally conductive material. Further, the inlet conduit 30 is in thermal exchange relationship with the temperature equilibrating rod 20.

In the preferred embodiment, the temperature equilibrating rod 20 extends from within the housing 14 and has one end 38 thereof proximate the flow cell 12 and the other end 40 distal the housing 14. The rod 20 is preferably characterized by a high thermal conductivity, for example copper, and is so positioned in the housing 14 that the one end 38 thereof is effectively in thermal equilibrium with the flow cell 12.

The equilibrating rod 20, in one embodiment, has coils 39 of the inlet conduit 30 wrapped around it, and in heat exchange relationship therewith. That is, the inlet conduit 30, after separating from the outlet conduit 34 and before being connected to the flow cell 12, is helically wrapped about the rod 20. Preferably, the inlet conduit 30 is bonded to the rod 20 by a thermally conductive material.

As shown in the drawing, the flow cell housing 14 is positioned in a cradle 42 suspended from the kinematic mounting mechanism 16 by a pair of rigid suspension rods 44. The cradle 42 provides an increased stability to the continuous alignment of the flow cell 12 and the remaining optical components. This increased stability is derived not only from the mass of the cradle 42 per se, but also from the accuracy of the positioning of the flow cell housing 14 therein. This accuracy is derived from the positioning of the flow cell housing 14 within the cradle 42 being accurately repeatable.

In addition, to avoid fracture and/or rupture of the conduits, 30 and 34, which are thin-walled and hence inherently fragile, a means 45, such as a rod, for supporting the conduits, 30 and 34, is provided between the housing 14 and the casting 46. Preferably, the rod 45 is stainless steel having a diameter of between about 1 and 2 mm. In the preferred embodiment, the rod 45 and the conduits, 30 and 34, are secured together by a snug flexible tubing, or the like.

In one specific application of the assembly 10, the kinematic mounting mechanism 16 includes a casting 46 defining a portion 48 of the an optical enclosure 50. The enclosure 50 is positioned within an external, or outer, cabinet 52 of, for example, a liquid chromatographic detector.

In this application the inlet fitting 28 is connected to receive the eluate of a chromatographic separating column, not shown. The outlet fitting 32 is connected to deliver the exiting fluid to a waste vessel, not shown. In order to minimize band dispersion and maximize the thermal energy transfer the inlet conduit 30 preferably has an inside diameter on the order of about 0.13 mm and an outside diameter on the order of about 0.25 mm. The minimizing of the band dispersion and the maximizing of the heat transfer are substantially due to the radial flow mixing of the fluid in the relatively small diameter inlet conduit 30. The outlet conduit 34 is not so restricted with regard to the inside diameter thereof since the band dispersion of the exiting fluid does not influence the measurement. However, the external diameter of the outlet conduit 34 does significantly contribute to the amount of heat exchanged between itself and the inlet conduit 30. This contribution is derived from the available surface area of the outlet conduit 34 which can be contacted by the inlet conduit 30. In the case where the inlet and outlet conduits, 30 and 34 respectively, are stainless steel and the lead angle of the helix of the wrapping is between 60 to 70 degrees the outlet conduit 34 should have an inside diameter of about 0.3 mm and an outside diameter of about 0.63 mm.

Although the exact location of the outlet fitting 32 and the outlet port 26 of the flow cell 12 can vary considerably, the length of both the inlet conduit 30 and the outlet conduit 34 should be minimized. The inlet conduit 30 preferably passes directly from the input fitting 28 to the nearest point of the outlet conduit 34. In this manner the length of outlet conduit 34 over which the inlet conduit of 30 is wrapped is maximized. At the point along the outlet conduit 34 which is closest the member 36 the inlet conduit 30 departs the outlet conduit 34 and wraps about the member 36. In the preferred embodiment, the rod 20 is made of copper and has an outside diameter of about 0.62 cm and extends from the housing by a length of about 1.3 cm.

In the preferred embodiment the inlet conduit 30 is bonded to the outlet conduit 34 and the rod 20 using a thermally conductive adhesive such as, for example, silver-filled epoxy resin.

The counterflow heat exchange between the fluid entering the inlet fitting 28 and the fluid exiting the outlet fitting 32, and the thermal equilibration of the incoming stream with the flow cell body 12 are inherent in the present assembly 10 regardless of the temperature of the eluate from the separating column.

In the present assembly 10, the inlet conduit 30 is wrapped about the outlet conduit 34 whereby, because of the inherent temperature differential discussed above, a small temperature gradient is initially formed between the "higher temperature" inlet conduit 30 and the "lower temperature" outlet conduit 36 which is approximately uniform along their entire wrapped length. Under operational conditions, a steady state is achieved whereat the entering fluid loses heat and the exiting fluid gains heat at an equal rate whereby the fluids achieve a small temperature difference both at inlet port 24 and exit port 26, where they enter and leave the assembly, and also at the point where inlet conduit 30 leaves exit conduit 34 to go to rod 20.

Advantageously, under the conditions of the preferred embodiment, discussed above, any perturbations in the temperature of the entering fluid are rapidly attenuated by the counterflow heat exchange between inlet conduit 30 and exit conduit 34 where they are wrapped. The remaining small temperature difference and perturbation is rapidly equilibrated via the thermally conductive rod 20 which brings the temperatures of the inlet fluid and of cell 12 very close together before the fluid enters the cell 12.

The combined effect of the small temperature difference provided by the counterflow heat exchanger and the effect of the equilibrating heat rod 20 in further reducing the temperature difference between incoming fluid and flow cell are necessary to achieve these advantages.

Under normal operating conditions, there is only a relatively small temperature difference between the fluid entering inlet port 24 and that leaving outlet port 26. This shows that excess heat or heat deficit carried into assembly 10 by the entering fluid is nearly all removed by the exiting fluid, and hence is not transferred to either the flow cell or the main instrument structure. Therefore, changes in the temperature of the incoming fluid have only a small effect on the temperature of the flow cell.

Finally, since there is little heat transferred to the flow cell body 12 by the incoming fluid the cell body 12 can be relatively thermally isolated from the main structure of the instrument by the rigid suspension rods 44. Thus, the temperature thereof must move only a small amount from the temperature of the main instrument structure toward that of the fluid entering at the inlet port 24 in order to dissipate that heat to the main instrument structure. Hence, the temperature of the cell 12 does not approach that of the incoming fluid to come into thermal equilibrium with that fluid.

The present invention has been described by use of an embodiment which is exemplary only and which is not deemed to be limiting. Thus, the present invention is limited only by the appended claims and the reasonable interpretation thereof.

What is claimed is:

1. In a liquid chromatograph a thermal equilibrating apparatus for equilibrating the temperature of liquid as it passes through a flow cell comprising, in combination:

a flow cell housing having an inlet port and an outlet port through which liquid can pass from said inlet port to said outlet port;

an outlet conduit in fluid communication with said outlet port for conducting away fluid exiting from said outlet port;

an inlet conduit coupled to said inlet port and of a smaller diameter than said outlet conduit for conducting fluid into said inlet port, said inlet conduit being coiled around and in thermal transfer relationship with said outlet conduit along a portion of the length thereof; and means in direct thermal transfer relationship with said flow cell housing around which said inlet conduit is coiled in a thermal transfer relationship therewith and disposed between the point of separation of said inlet conduit from said outlet conduit and the connection of said inlet conduit to said inlet port.

2. Apparatus as claimed in claim 1 wherein said thermal transfer effecting means includes a member having one end thereof within said housing and another end thereof external said housing and distal said flow cell.

3. Apparatus as claimed in claim 2 wherein said member is a rigid copper rod.

4. Apparatus as claimed in claim 1 wherein said helically coiled portion of said inlet conduit about said thermal transfer means has a lead angle in the range of 60 to 70 degrees with respect to the axis of said thermal transfer means.

5. Apparatus as claimed in claim 1 wherein said inlet conduit is helically wrapped around and in contact with said outlet conduit.

6. Apparatus as claimed in claim 5 wherein said inlet conduit is helically coiled about said outlet conduit, said coiling lead angle is in the range of 60 to 70 degrees with respect to the axis of said outlet conduit whereby thermal transfer is effected therebetween.

* * * * *